(12) United States Patent
Kaufmann

(10) Patent No.: US 11,759,112 B2
(45) Date of Patent: Sep. 19, 2023

(54) CATHETER DEVICE FOR PLACING A SENSOR

(71) Applicant: BIOTRONIK SE & Co. KG, Berlin (DE)

(72) Inventor: Ralf Kaufmann, Loerrach (DE)

(73) Assignee: BIOTRONIK SE & Co. KG, Berlin (DE)

( * ) Notice: Subject to any disclaimer, the term of this patent is extended or adjusted under 35 U.S.C. 154(b) by 657 days.

(21) Appl. No.: 16/946,149

(22) Filed: Jun. 8, 2020

(65) Prior Publication Data
US 2020/0390341 A1 Dec. 17, 2020

(30) Foreign Application Priority Data
Jun. 13, 2019 (EP) ..................................... 19179895

(51) Int. Cl.
*A61B 5/00* (2006.01)
*A61B 5/0215* (2006.01)

(52) U.S. Cl.
CPC .......... *A61B 5/0215* (2013.01); *A61B 5/6852* (2013.01); *A61B 5/6869* (2013.01); *A61B 5/6876* (2013.01); *A61B 2560/04* (2013.01); *A61B 2560/066* (2013.01)

(58) Field of Classification Search
CPC .......... A61B 2560/04; A61B 2560/066; A61B 5/0215; A61B 5/6852; A61B 5/6869; A61B 5/6876
See application file for complete search history.

(56) References Cited

U.S. PATENT DOCUMENTS

| 2012/0108986 | A1* | 5/2012 | Beasley | A61B 5/6879 |
| | | | | 600/486 |
| 2015/0273212 | A1 | 10/2015 | Berthiaume et al. | |
| 2016/0279423 | A1 | 9/2016 | Kelly et al. | |
| 2018/0168468 | A1* | 6/2018 | Kelly | A61B 5/02152 |

OTHER PUBLICATIONS

E. Y. Chow, "Fully Wireless Implantable Cardiovascular Pressure Monitor Integrated with a Medical Stent", IEEE Transactions on Biomedical Engineering, vol. 57, No. 6, 2010.
(Continued)

*Primary Examiner* — Eric J Messersmith
(74) *Attorney, Agent, or Firm* — Buchanan Ingersoll & Rooney PC

(57) ABSTRACT

A catheter device for placing a sensor device comprises a shaft and a coupling device, arranged at the shaft, for coupling the catheter device to the sensor device comprising at least one bracket element. The coupling device comprises a coupling element and a locking element adjustable with respect to the coupling element, wherein the coupling element comprises at least one engagement section with which the at least one bracket element of the sensor device can be brought in engagement, wherein the locking element is designed, in a coupled position, to block the at least one bracket element at the at least one engagement section, and is adjustable with respect to the coupling element so as to release the at least one bracket element for detachment from the at least one engagement section.

14 Claims, 17 Drawing Sheets

(56) References Cited

OTHER PUBLICATIONS

European Search Report and Annex to the European Search Report on European Patent Application No. EP 19 17 9895.8, dated Dec. 10, 2019 (7 pages).
J.H. Dreyfuss et al., "Prevent the Next Heart Attack: Implant a CardioMEMS Device in a Heart Failure Patient," M.D./alert, Feb. 2016.
P. B. Adamson et al., "Champion* Trial Rational and Design: The Long-Term Safety and Clinical Efficacy of a Wireless Pulmonary Artery Pressure Monitoring System", Journal of Cardiac Failure, vol. 17, No. 1, 2011.

* cited by examiner

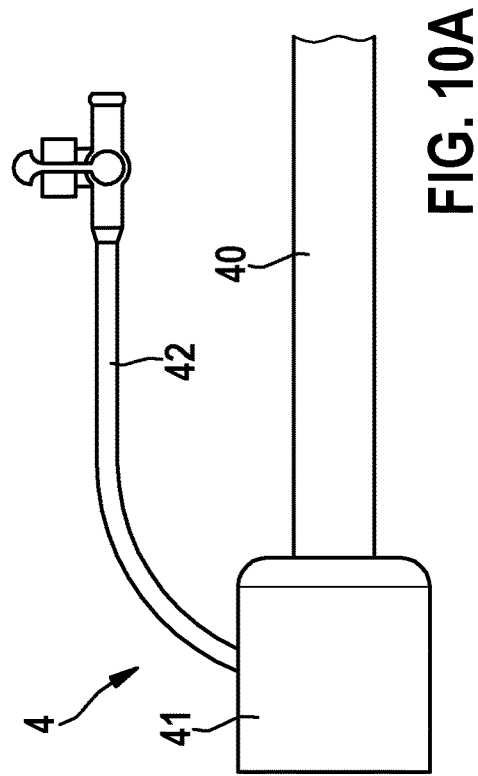
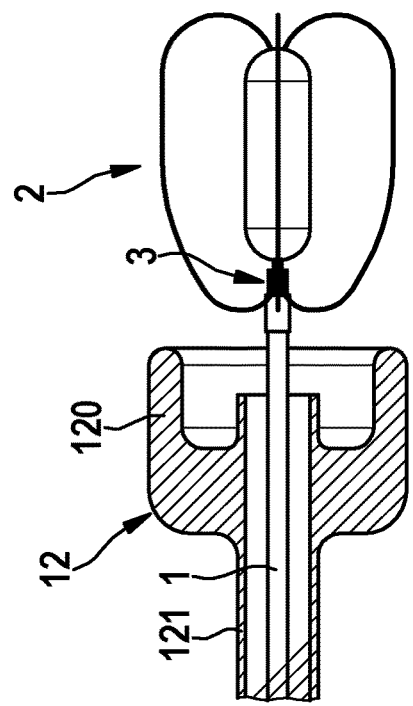

CATHETER DEVICE FOR PLACING A SENSOR

CROSS-REFERENCE TO RELATED APPLICATIONS

This patent application claims the benefit of and priority to co-pending European Patent Application No. EP 19179895.8, filed on Jun. 13, 2019 in the European Patent Office, which is hereby incorporated by reference in its entirety.

TECHNICAL FIELD

The present invention relates to a catheter device for placing a sensor device, and to a system comprising a catheter device and a sensor device.

BACKGROUND

Such a catheter device comprises a shaft and a coupling device, arranged at the shaft, for coupling the catheter device to the sensor device comprising at least one bracket element.

Such a catheter device can be used, for example, as a delivery catheter for the placement of a sensor device in the human heart or in another blood vessel. A sensor device of the type in question here may be designed, for example, as a pressure sensor, a temperature sensor, an oxygen sensor or a flow sensor, and is to record measuring data inside a patient and transmit the data to an external device by way of telemetry, for example. Such sensor devices can be used, for example, within the scope of so-called home monitoring of seriously ill patients so as to enable patient monitoring and care in an ambulatory environment.

Sensor devices that can be placed in a patient atraumatically, i.e., in a manner that minimizes injury of a vessel wall, are desirable. The placement by way of the catheter device is to be possible easily, flexibly and reliably in the process.

Implantable sensor devices for monitoring pressure in the human heart are described, for example, in the articles J. H. Dreyfuss et al., "Prevent the Next Heart Attack: Implant a CardioMEMS Device in a Heart Failure Patient," M.D./alert, February 2016; P. B. Adamson et al., "Champion* Trial Rational and Design: The Long-Term Safety and Clinical Efficacy of a Wireless Pulmonary Artery Pressure Monitoring System", Journal of Cardiac Failure, Vol. 17, No. 1, 2011; and E. Y. Chow, "Fully Wireless Implantable Cardiovascular Pressure Monitor Integrated with a Medical Stent", IEEE Transactions on Biomedical Engineering, Vol. 57, No. 6, 2010.

The present invention is directed at overcoming one or more of the above-mentioned problems.

SUMMARY

It is an objective to provide a catheter device for placing a sensor device, and a system comprising a catheter device and a sensor device, which allow a sensor device to be placed easily, flexibly and reliably. If necessary, renewed gripping of the sensor device for correcting a sensor position or for removing the sensor device is to be made possible.

At least this objective is attained by a subject matter having the features of claim 1.

According to this, the coupling device comprises a coupling element and a locking element adjustable with respect to the coupling element. The coupling element comprises at least one engagement section with which the at least one bracket element of the sensor device can be brought in engagement, wherein the locking element is designed, in a coupled position, to block the at least one bracket element at the at least one engagement section, and is adjustable with respect to the coupling element so as to release the at least one bracket element for detachment from the at least one engagement section.

The catheter device uses a coupling device to establish a coupling to a sensor device to be implanted. The sensor device can be gripped by way of the coupling device, so that, in a coupled position, the sensor device is fixedly connected to the catheter device.

The coupling is established in the process by the sensor device, in the coupled position, engaging with one or more bracket elements in one or more engagement sections of a coupling element of the coupling device. The engagement sections can be formed in the manner of undercuts, for example, and can thus establish a form-fit connection between the sensor device and the coupling device. The form-fit connection is blocked by way of a locking element in such a way that the bracket elements of the sensor device, in the coupled position, cannot become readily, at least not without actuation of the locking element, disengaged from the engagement sections of the coupling element, but are held in a reliable and robust manner at the catheter device by way of the coupling device.

In the coupled position, the sensor device can be implanted in a patient by way of the catheter device and, for this purpose, be moved to a predetermined location in the human heart or in another vessel. Once the intended location has been reached, the locking element can be actuated so as to release the bracket elements of the sensor device, and thereby allow the sensor device to be detached from the coupling device, and thus from the catheter device.

The coupling can be undone by adjusting the locking element using a comparatively small stroke. By adjusting the locking element, the at least one engagement section of the coupling element is released so that the at least one bracket element of the sensor device can be easily disengaged from the engagement section.

The locking element is used to block the at least one bracket element, when it is engaged with the at least one engagement section of the coupling element, in such a way that the at least one bracket element cannot become disengaged from the engagement section. In a blocking position, the locking element, for this purpose, has such a spatial positional relationship with respect to the engagement section that the bracket element cannot be removed from the engagement section. Only when the locking element has been actuated for detaching the coupling the bracket element can be removed from the assigned engagement section, and the sensor device can be decoupled from the catheter device.

The coupling device can be designed to have a comparatively small installation space, which makes it possible to use a catheter device comprising a thin shaft (for example, a diameter of 6 F or 7 F, or 1.8 mm to 2.4 mm).

In one embodiment, the coupling element is fixedly connected to a section of the shaft, for example, in the region of a distal end of the shaft. For establishing the coupling, the at least one engagement section is formed at the coupling element in such a way that the sensor device can be easily and reliably brought in engagement with the engagement section by way of the at least one bracket element and, in a coupled position, is locked to the coupling element by way of the locking element.

In one embodiment, the locking element is linearly adjustable, for example, along an actuating direction with respect to the coupling element. The coupling element may be guided to the locking element along the actuating direction, so that the locking element can be adjusted between a blocking position for blocking the at least one bracket element in engagement with the at least one engagement section of the coupling element, and a detachment position for releasing the sensor device.

In one embodiment, the coupling element comprises a distal rim, which is located away from the shaft and which extends, for example, along a plane oriented transversely with respect to the longitudinal extension direction of the shaft and is formed circumferentially at the coupling element designed, for example, in a sleeve-shaped manner. In one embodiment, at least one recess is formed, particularly integrally formed, in the rim, at which the at least one engagement section is formed in the manner of an undercut. Each bracket element of the sensor device can thus be coupled to the coupling element by engagement in the recess and the engagement section formed at the recess, wherein, in the coupled position, the engagement of the bracket element in the engagement section of the coupling element is blocked by way of the locking element in such a way that the bracket element cannot be readily, at least not without actuation of the locking element, disengaged from the engagement section.

In one embodiment, the locking element includes at least one engagement groove for receiving the at least one bracket element in the coupled position. For example, the locking element may comprise a body that is inserted in the sleeve-shaped coupling element and, with a distal end face, points outwardly in the distal direction. One or more engagement grooves may be formed at this distal end face in such a way that, in the coupled position of the sensor device, each bracket element of the sensor device engages in an engagement groove of the locking element. The engagement grooves may extend radially with respect to the (linearly oriented) actuating direction, for example, and, in the coupled position of the sensor device, are aligned with the engagement section in such a way that each bracket element is blocked with respect to the particular assigned engagement section as a result of engagement in the engagement groove, and thus cannot be disengaged from the engagement section.

In one embodiment, the coupling device comprises a pulling element, which is connected to the locking element and extends along the shaft, for adjusting the locking element. The pulling element is used to actuate the locking element and can be subjected to tensile loading so as to thereby adjust the locking element in the actuating direction with respect to the coupling element. For example, the pulling element may extend from the coupling device to a handle arranged at the proximal end of the shaft and may be coupled to an actuating element of the handle in such a way that, as a result of the actuation of the actuating element, a tensile force is exerted on the pulling element, and the locking element can thereby be adjusted in the actuating direction relative to the coupling element of the coupling device.

While the coupling device for coupling to the sensor device is arranged at the distal end of the shaft of the catheter device which is to be introduced into the body of a patient, the handle is arranged at the proximal end of the shaft of the catheter device, and can thus be actuated outside the body of the patient, so as to undo the coupling between the sensor device and the coupling device, after the sensor device has been placed as intended in the patient, or, if necessary, so as to grip the sensor device again for correcting the position of the sensor device or for removing the sensor device from the patient. For example, the actuating element may be rotatable at the handle so as to act on the pulling element for adjusting the locking element, wherein the handle, for example, comprises an anti-turn mechanism, which prevents an inadvertent actuation of the actuating element, and thus an inadvertent detachment prior to the intended placement of the sensor device.

In one embodiment, the coupling device comprises an elastic element, which is arranged at the coupling element and acts between the coupling element and the locking element. For example, the elastic element may interact with a conical section formed at the body of the locking element in such a way that the elastic element is elastically deformed during an adjustment of the locking element in the actuating direction for undoing the coupling between the sensor device and the coupling device, and exerts elastic counter tension, counter to the actuating direction, on the locking element. In this way, it is possible to cause an automatic restoration of the locking element after the actuation has been carried out, so that the locking element automatically attains an initial position, corresponding to the coupling position, again when no tensile forces are exerted on the pulling element any longer.

In addition or as an alternative to the provision of an elastic pre-tension, the elastic element may be used to seal a transition between the coupling element and the shaft of the catheter device. For example, the elastic element may be arranged at a bottom section of the coupling element, which extends transversely to the actuating direction and separates a receiving space of the coupling element, in which the locking element is adjustably accommodated, from the shaft of the catheter device. The bottom section may include an opening in the process, through which the pulling element is guided for actuation of the locking element, wherein the elastic element may be arranged, for example, in the manner of a sleeve in the region of the opening at the bottom section in such a way that a transition between the bottom section and the locking element, and thus the opening in the bottom section through which the pulling element is guided, is sealed in a moisture-proof manner.

The locking element faces the bottom section with a side that faces away from the distal end face of the locking element which includes the at least one engagement groove. Upon an actuation of the locking element for undoing the coupling between the sensor device and the coupling device, the locking element is moved closer to the bottom section, wherein the elastic element is arranged between the locking element and the bottom section of the coupling element in such a way that the elastic element, during an adjustment of the locking element in the actuating direction, is elastically deformed, but preferably maintains a moisture-proof seal between the locking element and the bottom section in the process.

The bottom section may moreover serve as a stop for the locking element, and thus define a maximum actuating travel for the locking element.

In one embodiment, the shaft comprises a deflectable shaft segment, at which the coupling device is arranged. The deflectable shaft segment is formed in the region of the distal end of the shaft and may be deflected in such a way that the catheter device can also be flexibly and controllably guided in anatomically wound vessels, for example to the pulmonary artery, for placing the sensor device.

The deflectable shaft segment may, for example, be actuated by way of the same actuating element at the handle by way of which also the pulling element of the coupling device can be actuated. While the actuation of the pulling element for the adjustment of the locking element may take place, for example, by a rotation of the actuating element at the handle, a deflection of the deflectable shaft segment can be carried out, for example, by a linear adjustment of the actuating element at the handle.

A system comprises a catheter device according to the above-described type and a sensor device to be coupled to the coupling device of the catheter device. Such a sensor device may be designed, for example, as a pressure sensor, a temperature sensor, an oxygen sensor or a flow sensor, and comprises, for example, a dedicated power supply unit, such as a battery, and a communication device, for example, for data transmission by way of telemetry, so that the sensor device in the human patient can self-sufficiently take over monitoring tasks, in the implanted state, and transmit data signals to an external device.

Such a sensor device comprises, for example, a sensor housing and one or more bracket elements arranged at the sensor housing, which, in the coupled position, are engaged with assigned engagement sections of the coupling element, and thus establish a fixed (but detachable) connection between the sensor device and the catheter device. The bracket elements are preferably formed of a highly elastic material and extend at the sensor housing in such a way that the sensor device can be placed atraumatically, i.e., in a manner that causes minimal injury of the vessel wall, in a vessel.

For example, each bracket element may be attached with a first end to a distal side of the sensor housing, and with a second end to a proximal side of the sensor housing which faces away from the distal side. The bracket element is thus fixedly connected with both ends to the sensor housing and forms a loop that protrudes from the sensor housing. In particular in the region of the proximal end of the sensor housing, the coupling device may engage on the bracket elements so as to establish a connection between the sensor device and the catheter device.

For example, the sensor device can comprise three identically configured bracket elements, which are uniformly distributed around the sensor housing. The sensor housing can be held approximately centrally (seen in a cross-sectional plane perpendicularly to a longitudinal extension direction of the sensor housing which is directed from proximal to distal) between the bracket elements in the process, and can be supported by way of the bracket elements, in an implanted position, in such a way on surrounding vessel walls that the sensor housing is held approximately centrally in the vessel.

However, it is also conceivable for the bracket elements to be configured differently, and for the sensor housing, in the implanted position, to not be centrally supported in a vessel, but, for example, to be close to or even in contact with a vessel wall.

Further features, aspects, objects, advantages, and possible applications of the present invention will be explained in more detail and will become apparent with respect to exemplary embodiments and examples described below, in combination with the accompanying Figures and the appended claims

DESCRIPTION OF THE DRAWINGS

The idea underlying the present invention shall be described in greater detail hereafter based on the exemplary embodiments shown in the Figures. In the drawings:

FIGS. 10A-10J show views of the catheter device in cooperation with a sheath for the placement of the sensor device in the vessel of a patient.

DETAILED DESCRIPTION

Figure 1:
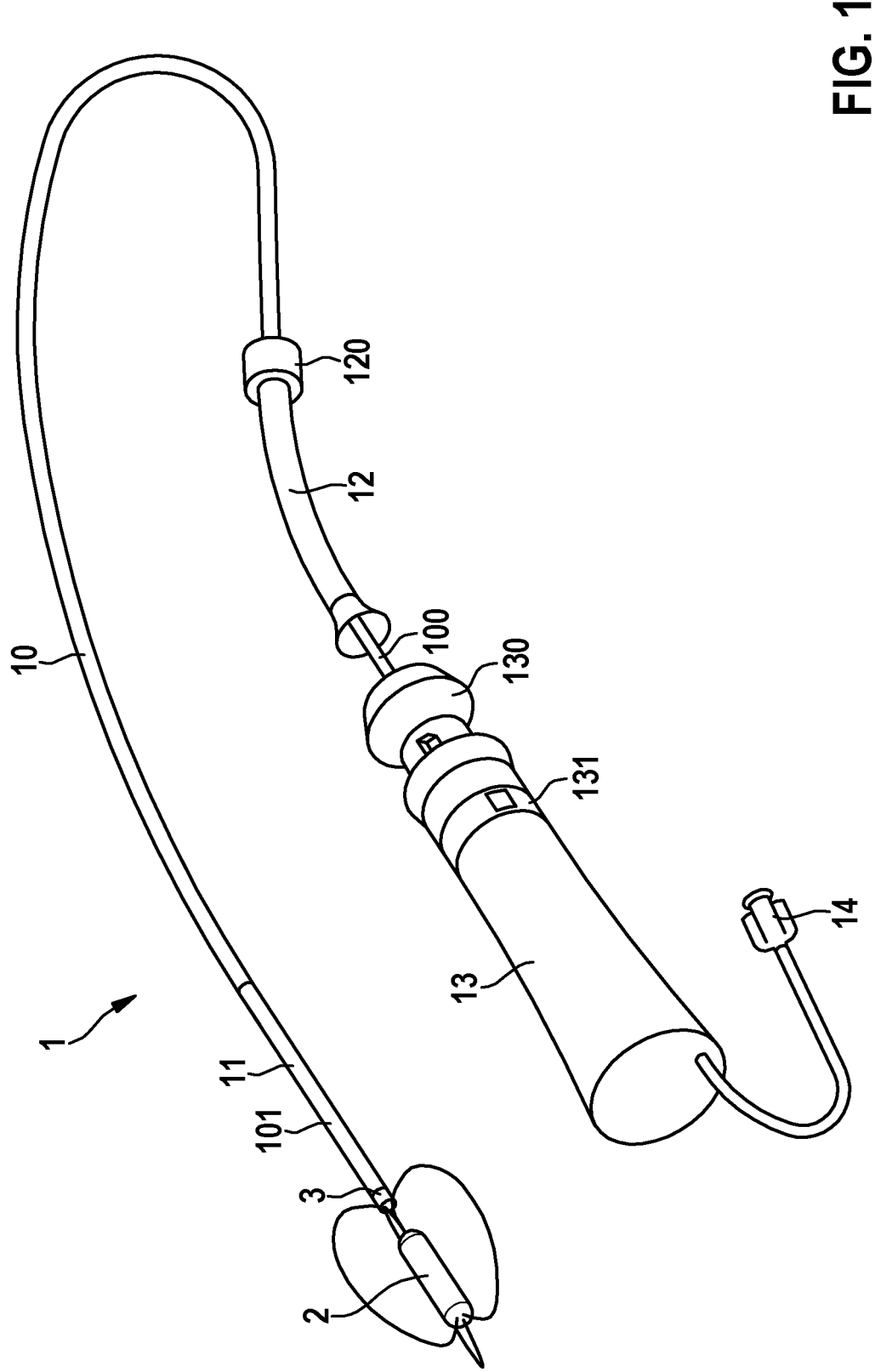
FIG. 1 shows a view of an exemplary embodiment of a catheter device, including a sensor device coupled to the catheter device.

A catheter device 1 illustrated in FIG. 1 comprises a shaft 10, which at a proximal end 100 is connected to a handle 13, and at a distal end 101 comprises a coupling device 3 for coupling to a sensor device 2. The catheter device 1 is used to implant the sensor device 2 in a vessel of a patient, for example, in a human heart or in another blood vessel, so as to implant the sensor device 2 designed, for example, as a pressure sensor, a temperature sensor, an oxygen sensor or a flow sensor, for example, for use within the scope of home monitoring of a seriously ill patient.

Figure 2:
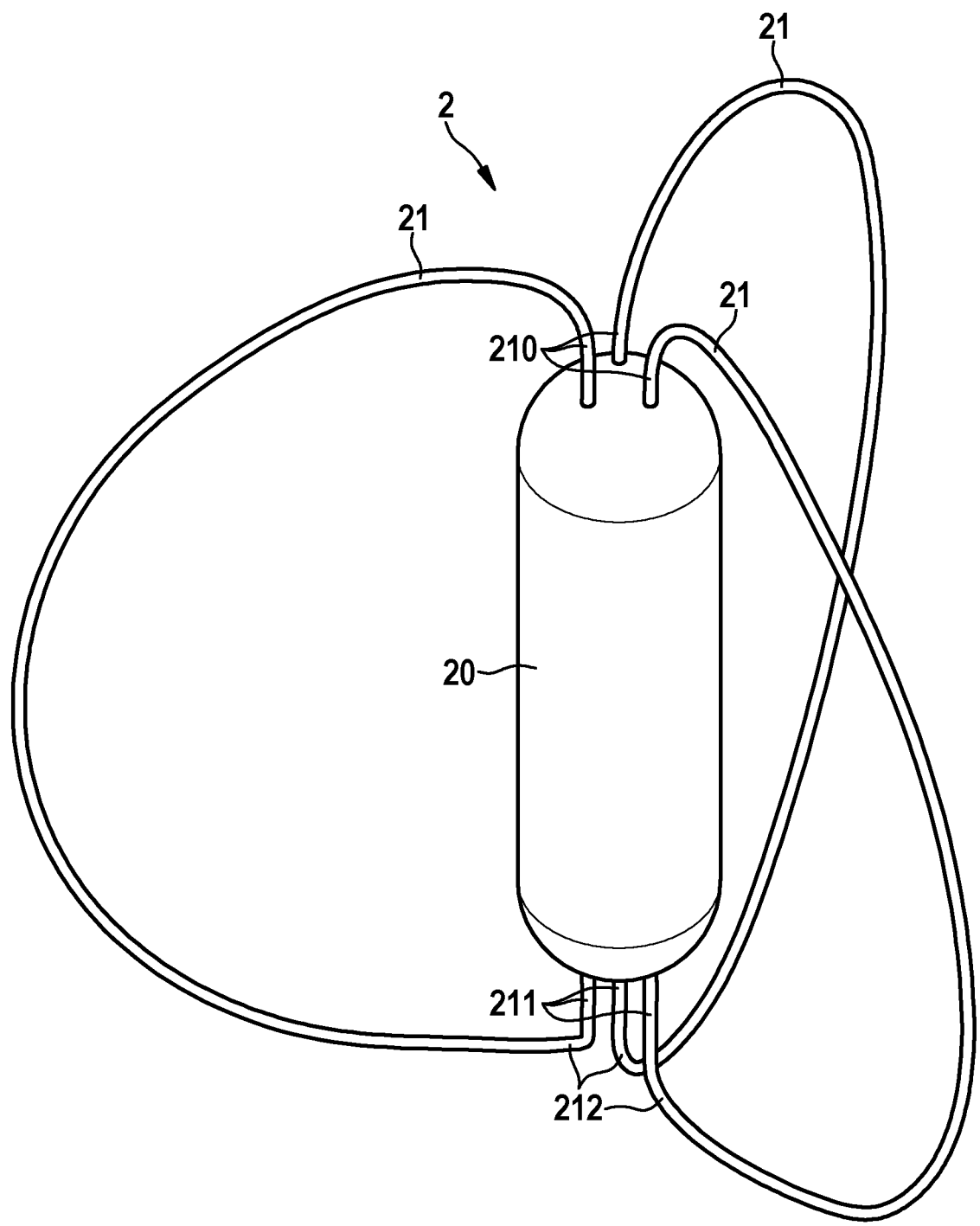
FIG. 2 shows a separate view of the sensor device.

The sensor device 2, shown in a separate view in FIG. 2, comprises a sensor housing 20, which can have a length of approximately 15 to 20 mm and a diameter of approximately 3 to 5 mm, for example, and encloses electrical and electronic components of the sensor device 2. For example, the sensor device 2 can comprise a dedicated power supply unit, in particular a battery, a suitable sensor system, a processor and a communication device for telemetric data transmission, so as to pre-process recorded sensor signals and transmit these to external devices.

In the illustrated exemplary embodiment, the sensor device 2 is designed as an atraumatic sensor, which can be implanted in a patient in a manner that causes minimal injury of the vessel wall. The sensor device 2 comprises bracket elements 21, manufactured in each case from a highly elastic wire, which are uniformly distributed around the sensor housing 20 and used to support the sensor housing 20 with respect to surrounding vessel walls when the sensor device 2 is implanted in a patient. The bracket elements 21 are each connected at one end 210 to a distal end of the sensor housing 20, and at the other end 211 thereof to a proximal end of the sensor housing 20, as is apparent from FIG. 2.

In the illustrated exemplary embodiment, the bracket elements 21 may also serve as antennas for communication by way of telemetry.

Figure 3:
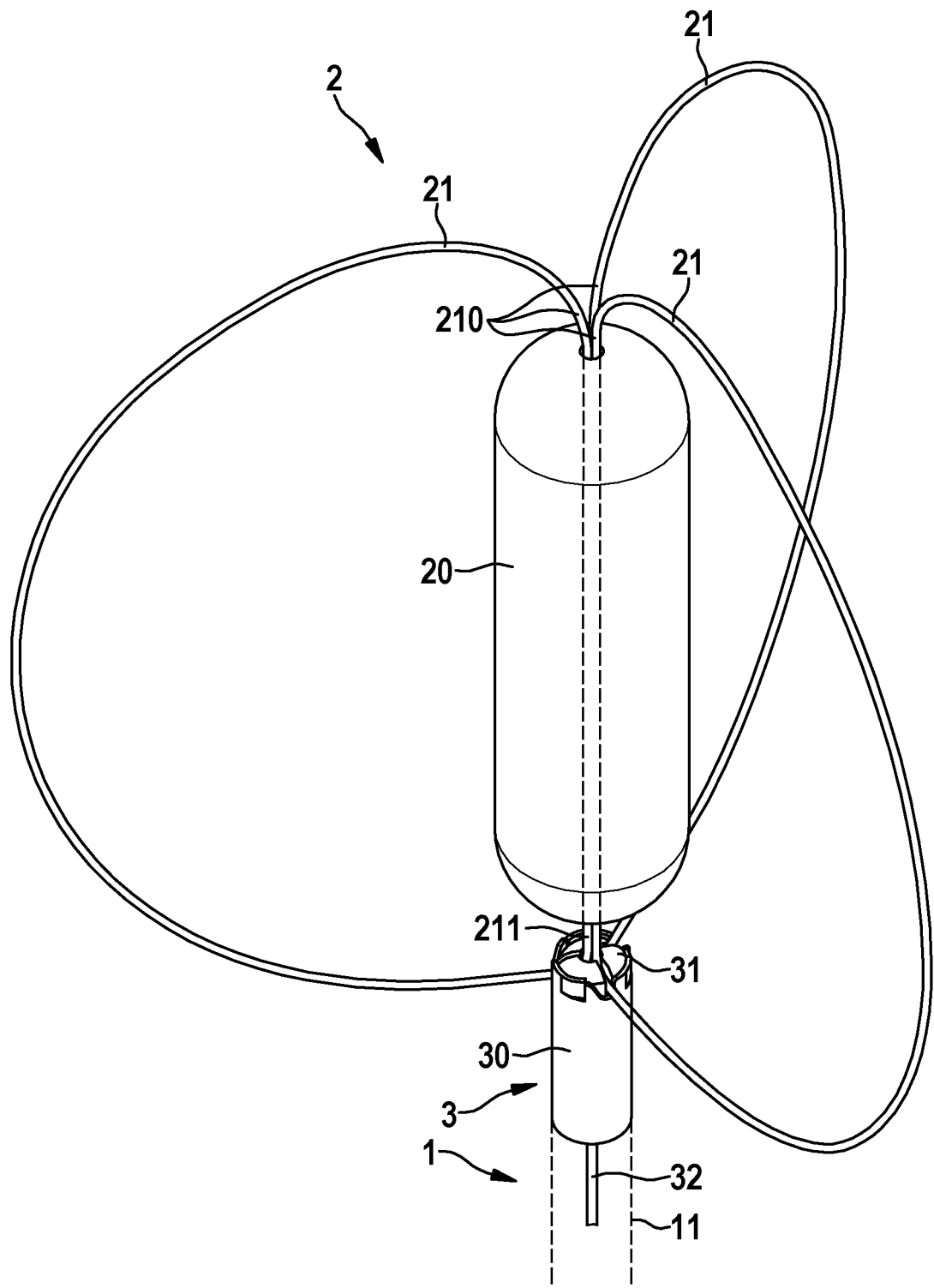
FIG. 3 shows a view of the sensor device at a coupling device of the catheter device.

The coupling device 3 of the catheter device 1 is used to establish a (detachable) connection between the catheter device 1 and the sensor device 2, so as to implant the sensor device 2 in a patient, using the catheter device 1. As is apparent from FIGS. 3 and 4, the coupling device 3, in a coupled position, establishes a connection between the catheter device 1 and the sensor device 2 by holding the bracket elements 21 of the sensor device 2 at the coupling device 3 by way of proximally formed anchor points 212 at the bracket elements 21 (see FIG. 2). When a coupling is present, the bracket elements 21 can be deployed, i.e., be in a state in which they are inserted in a human vessel in the implanted state.

In the region of the distal end 101, the shaft 10 comprises a deflectable shaft segment 11, which can be deflected so as to thereby also be able to guide the catheter device 1 through wound vessels. The coupling device 3 is arranged at the deflectable shaft segment 11 so that, during a deflection of the shaft segment 11, a sensor device 2 connected to the coupling device 3 is deflected together with the shaft segment 11.

The coupling device 3 comprises a coupling element 30 in the form of a sleeve, which is fixedly connected to the shaft segment 11 and, thereby, to the shaft 10, for example by adhesive bonding. A locking element 31 is accommodated inside the coupling element 30, which can be adjusted with respect to the coupling element 30 so as to release the sensor device 2 from the coupled position according to FIG. 4, and thereby enable a detachment of the sensor device 2 from the coupling device 3, and thus from the catheter device 1, as is illustrated in FIG. 5.

The coupling device 3 is illustrated in different views in FIGS. 6 to 9. Recesses 300 are integrally formed into the coupling element 30 at a distal rim 306 that is located away from the shaft 10, which each form an engagement section 302 in the manner of an undercut delimited to the outside by a blocking section 301. When the sensor device 2 is coupled to the coupling device 3, each bracket element 21 is inserted with an anchor point 212 in one of the engagement sections 302 and is thereby held in a form-locked manner at the coupling element 30.

The blocking section 301 protrudes transversely to a separation direction E (see FIG. 9) into the region of the respective assigned recess 300. The transition between the blocking section 301 and the recessed engagement section 302, which is delimited by the blocking section 301, extends obliquely with respect to the separation direction E here, as is also apparent in particular from FIG. 6.

Figure 4:
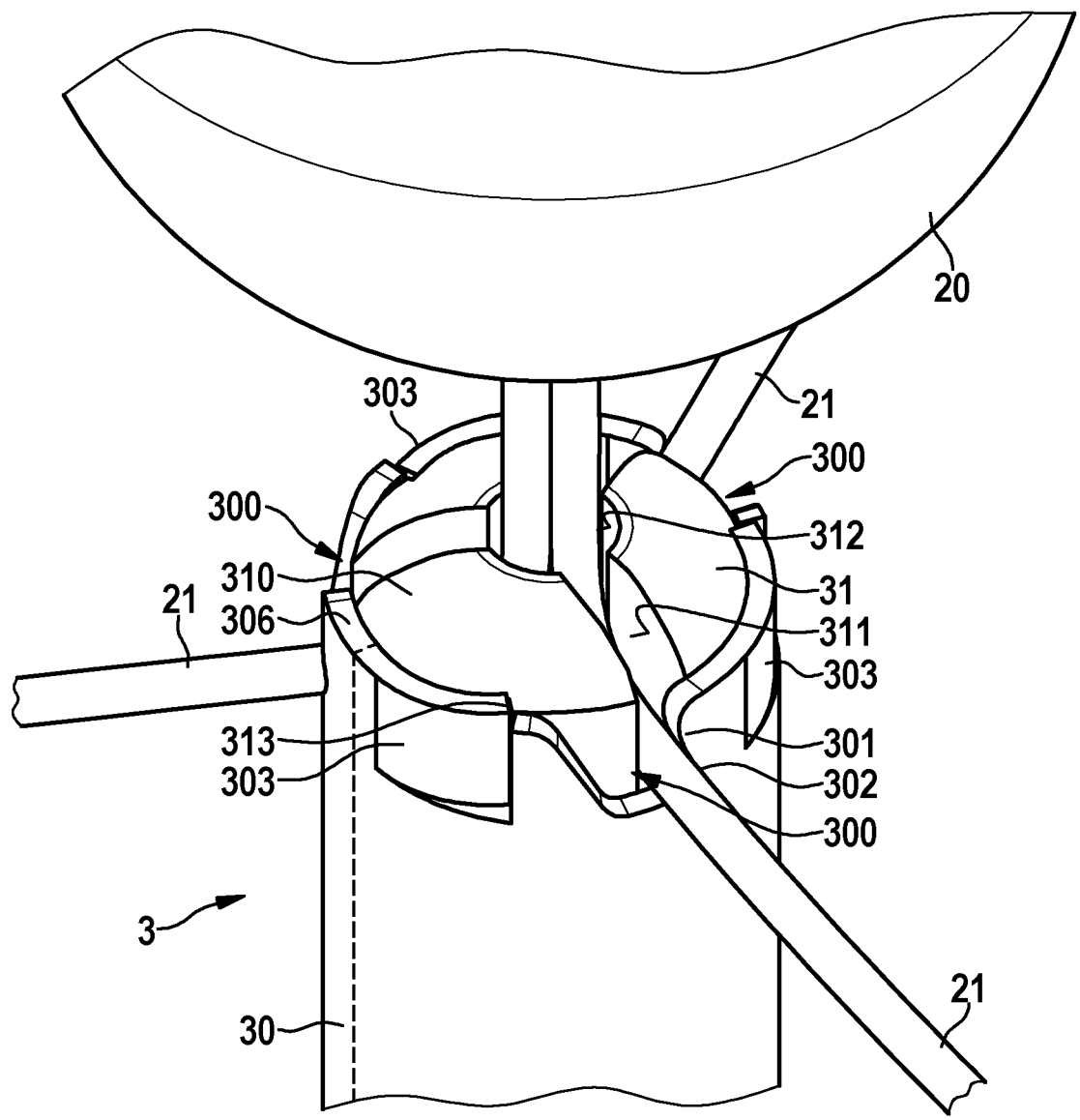
FIG. 4 shows a view of the sensor device at the coupling device, in a coupled position.
Figure 5:
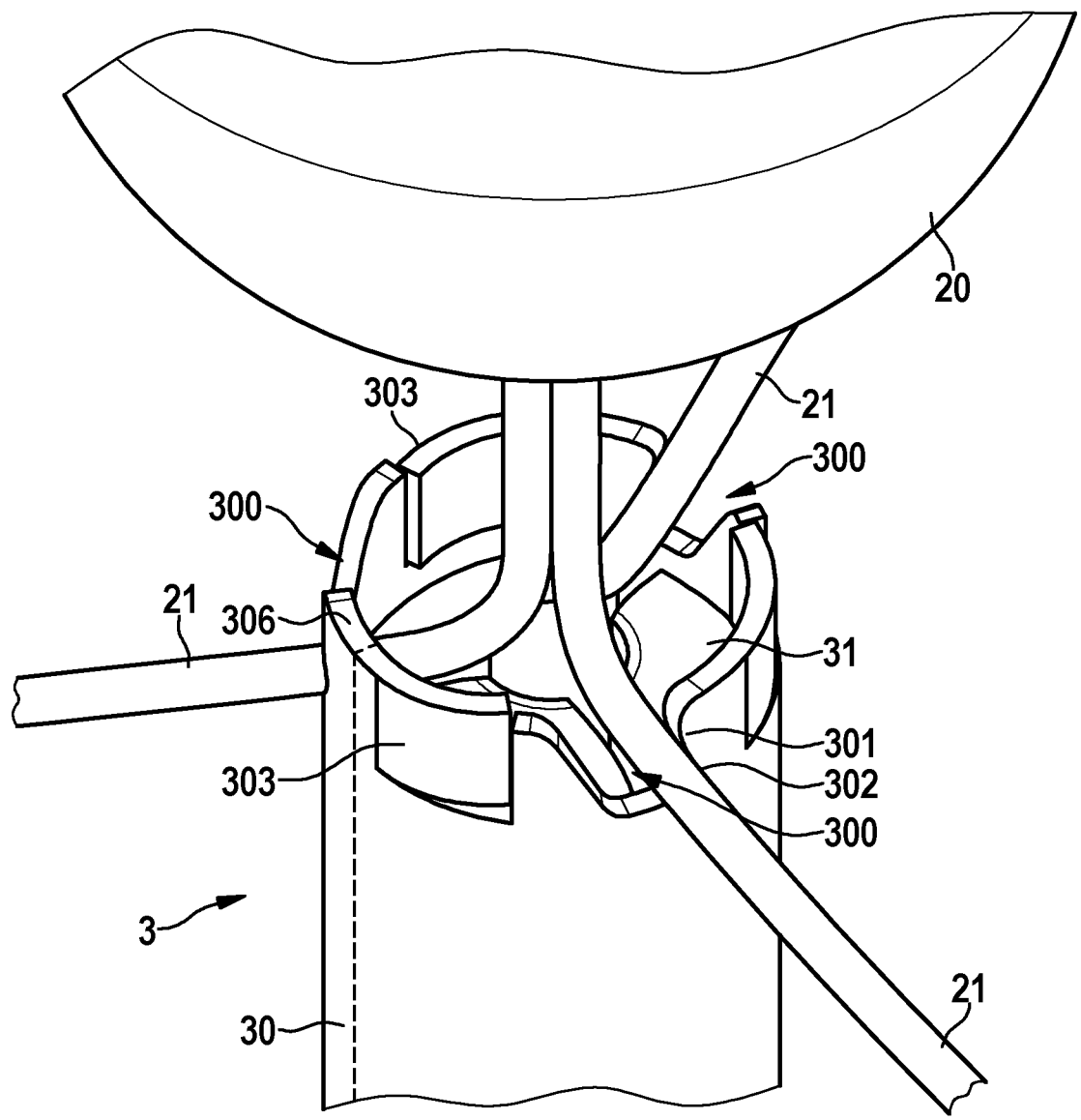
FIG. 5 shows a view of the sensor device at the coupling device, after actuation of a locking element of the coupling device for releasing the sensor device.
Figure 6:
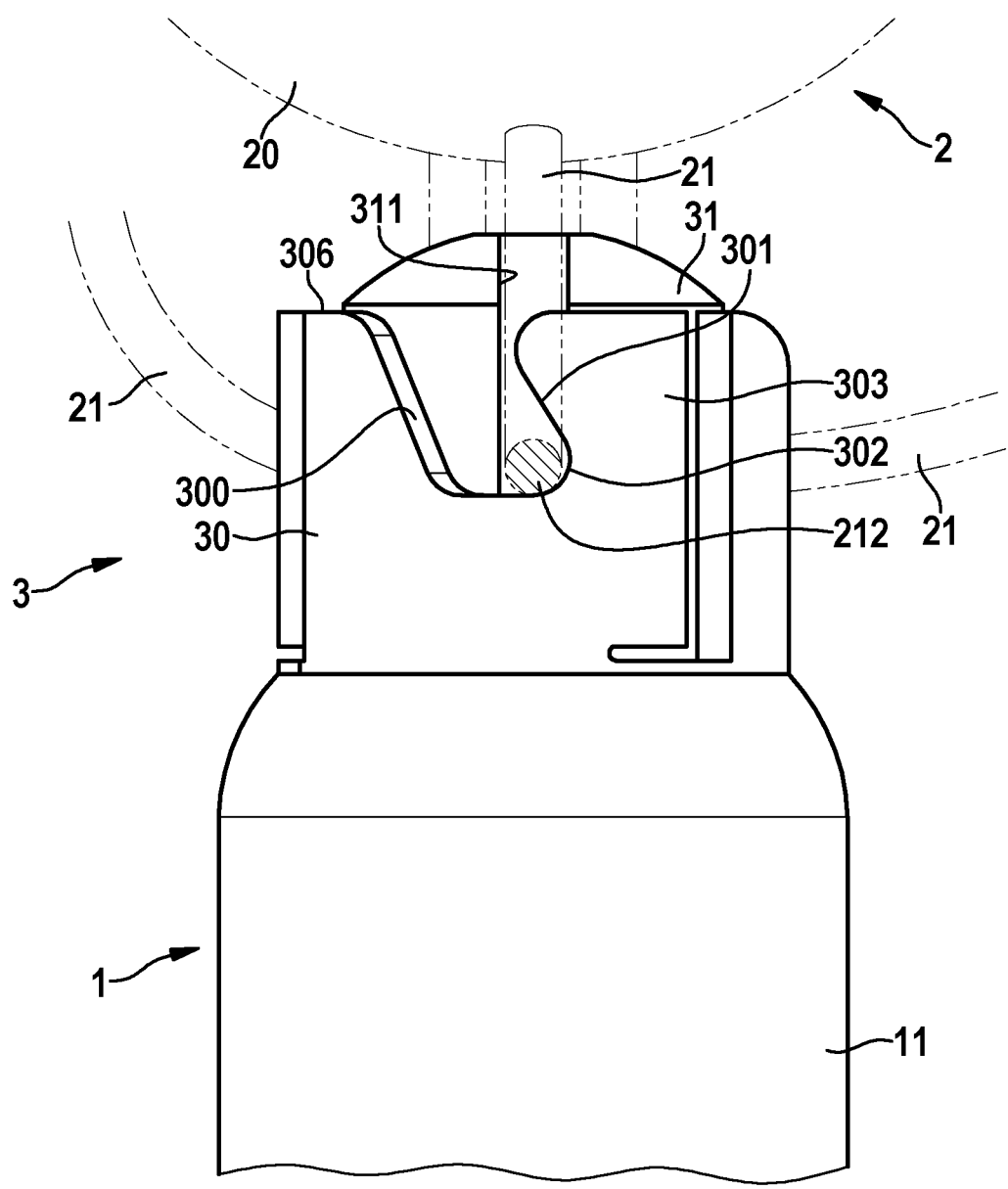
FIG. 6 shows a side view of the coupling device.
Figure 7:
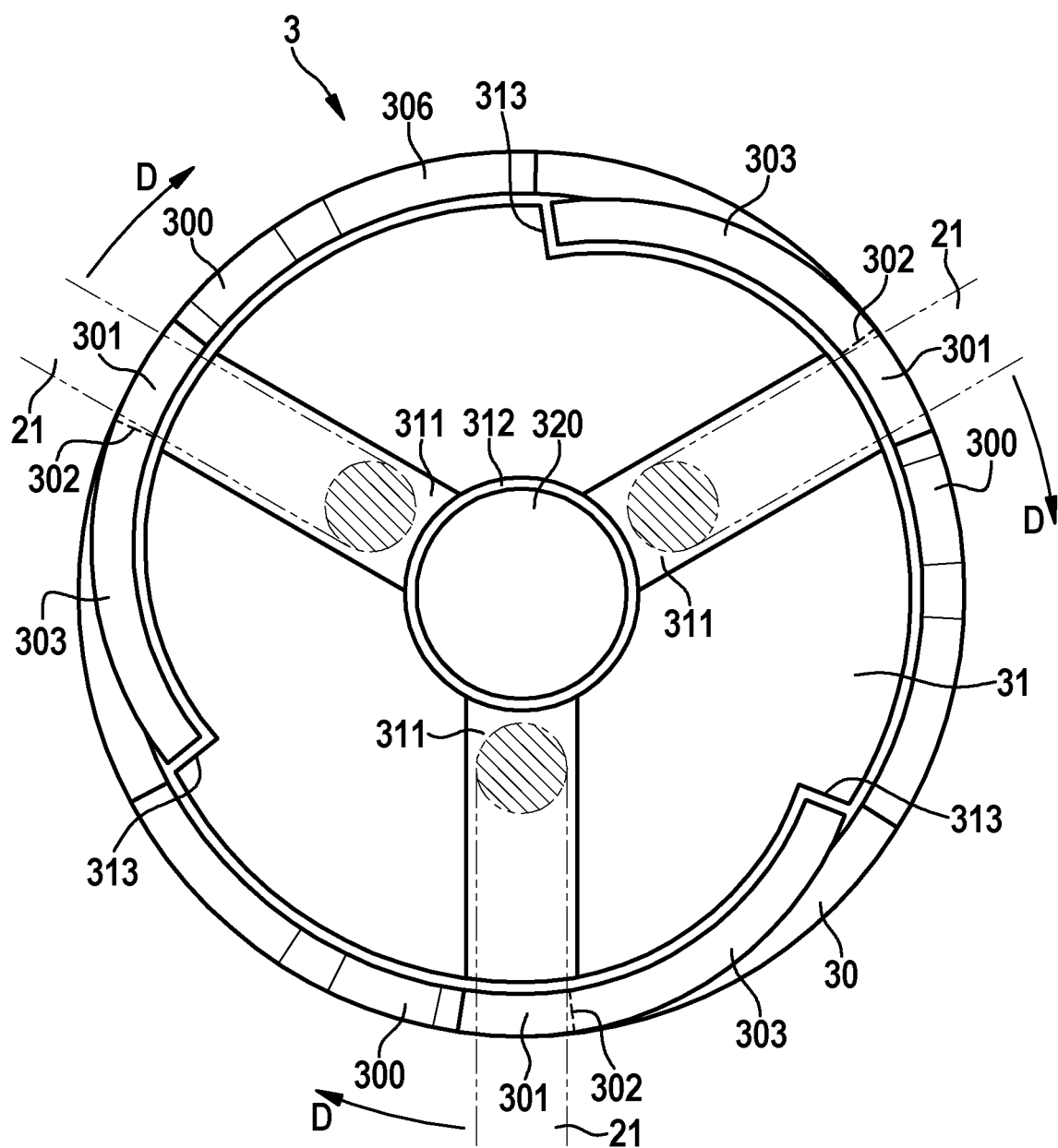
FIG. 7 shows a top view onto the coupling device.
Figure 8:
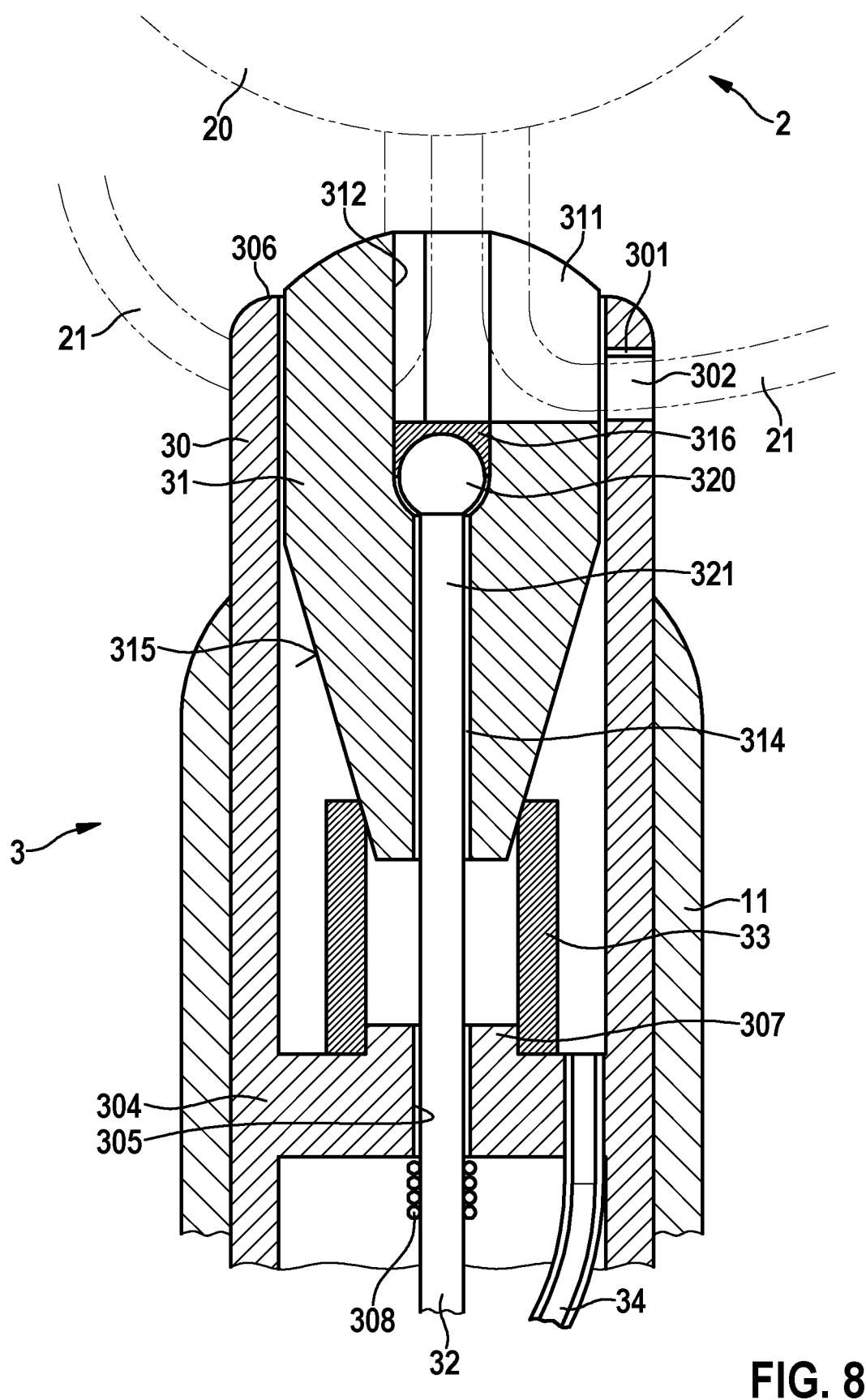
FIG. 8 shows a sectional view through the coupling device, in the coupled position.
Figure 9:
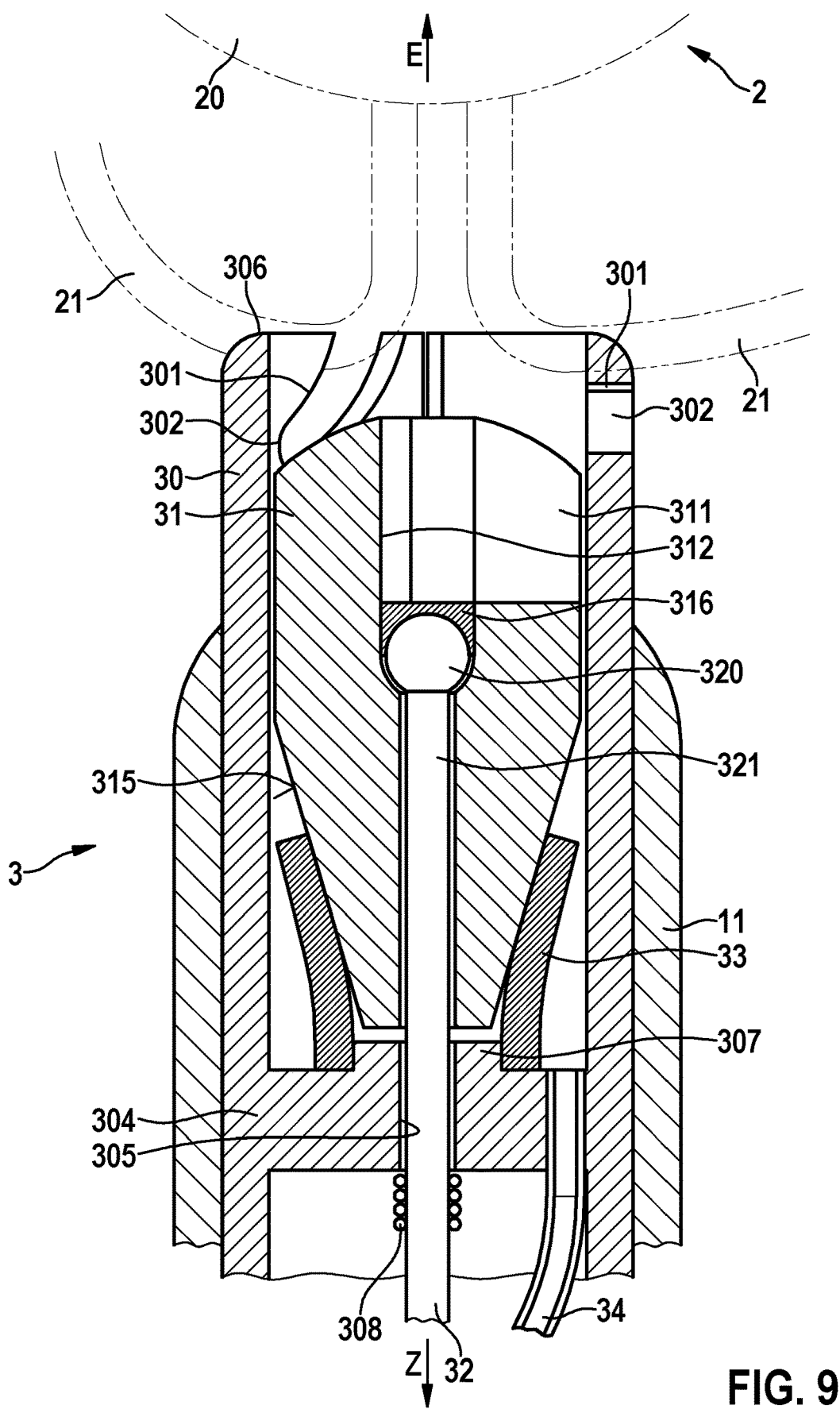
FIG. 9 shows a sectional view through the coupling device, in the release position.

The locking element 31 can be linearly adjusted along an actuating direction Z within the coupling element 30, as is apparent in the transition from FIG. 4 to FIG. 5, or from FIG. 8 to FIG. 9. The locking element 31 is guided in the coupling element 30 and comprises a body 310, at which engagement grooves 311 are formed on a distal, outwardly directed side, which are arranged in a star-shaped manner with respect to one another and open centrally into an opening 312, as is apparent from FIG. 4 and FIG. 7, for example. In the coupled position, each bracket element 21 of the sensor device 2 engages in one of the engagement grooves 311, wherein each engagement groove 311 is aligned with an assigned engagement section 302 of the coupling element 30, and the bracket element 21 is thereby blocked in the engagement section 302 as a result of the engagement of the respective bracket element 21 in the engagement groove 311, as is apparent, for example, from a combination of FIG. 4 and FIG. 6.

In the deflected state of the catheter, pulling on the pulling element 32 could primarily result in an amplification of the deflection or in a positioning error, instead of directly retracting the locking element 31 and releasing the sensor device 2. This is prevented by a compression spring 308 since, when the pulling element 32 is pulled, it acts as a stabilizing abutment against the bottom section 304. The locking element 31 is thus directly retracted, without any positioning error.

When the locking element 31 is adjusted in the actuating direction Z, the engagement grooves 311 are removed from the region of the engagement sections 302. As is apparent from FIG. 5, the bracket elements 21 thereby become disengaged from the engagement grooves 311, so that the bracket elements 21 are no longer blocked with respect to the engagement sections 302 and can be disengaged from the engagement sections 302 in a detachment direction D (see FIG. 7) by running against the oblique transition between the engagement sections 302 and the blocking sections 301. The sensor device 2 can thus be removed from the coupling device 3 along the separation direction E (see FIG. 9), without the bracket elements 21 being able to become interlocked in the recesses 300.

The locking element 31 is guided at the coupling element 30 along the actuating direction Z and is supported in a torsion-proof manner with respect to the coupling element 30, in particular in the coupled position (FIG. 4). For this purpose, the coupling element 30 comprises radially inwardly protruding stop elements 303, which each cooperate with an assigned stop 313 at the outer circumferential surface of the body 310 of the locking element 31 in such a way that a rotation of the locking element 31, in particular in the detachment direction D, with respect to the coupling element 30 is prevented.

The locking element 31 is connected to a pulling element 32, which with a spherical connecting element 320 is inserted in the central opening 312 of the locking element 31 and, with a section 321 extends through a longitudinally extending, tapered channel 314 of the locking element 31 which adjoins the opening 312, as is apparent from FIGS. 8 and 9. The pulling element 32 extends through an opening 305 in a bottom section 304 of the coupling element 30 and, along the shaft 10, to the handle 13, and is coupled on the side of the handle 13 to an actuating element 130.

The pulling element 32 is fixedly connected to the locking element 31 by way of the connecting element 320. The spherical connecting element 320 is glued to the locking element 31 by way of an adhesive compound 316 and is thereby fixedly connected, wherein the adhesive compound 316 moreover provides sealing of the channel 314 distally to the outside.

A sleeve-shaped (in a relaxed state, cylindrical) elastic element 33 is arranged between the locking element 31 and the bottom section 304 of the coupling element 30, in which a conical section 315 formed at the body 310 of the locking element 31 engages and which acts in an elastically pretensioning and sealing manner between the locking element 31 and the bottom section 304 of the coupling element 30. The elastic element 33, manufactured from an elastic, for example elastomeric, material is attached to a raised section 307 of the bottom section 304 (advantageously with circumferential pre-tension) and surrounds the opening 305, which is formed in the bottom section 304 and guides the pulling element 32, in such a way that the opening 305 is sealed in a moisture-proof manner to the outside. In particular, the elastic element 33 acts between the locking element 31 and the bottom section 304 in such a way that moisture from the outside cannot reach the region of the pulling element 32 and, thereby, the interior of the shaft 10 via the opening 305.

The elastic element 33 is additionally used to elastically restore the locking element 31 after the actuation has been carried out. During an adjustment of the locking element 31 in the actuating direction Z, the conical section 315 expands the elastic element 33 (see FIG. 8 in the transition to FIG. 9). When the tensile forces acting at the pulling element 32 subside, this elastic deformation of the elastic element 33 causes a restoring force on the locking element 31 counter to the actuating direction Z, in the direction of the initial position illustrated in FIG. 8, so that the locking element 31 is automatically restored into the initial position assigned to the coupled position.

This restoration can also support the separation of the sensor device 2 from the coupling device 3 in that the locking element 31 acts, with the distal end face thereof, on the bracket elements 21, and thereby pushes the sensor device 2 in the separation direction E away from the coupling device 3.

A rinsing line 34, which is used to rinse an interior space of the coupling element 30, opens into the bottom section 304 of the coupling element 30. In particular in the coupled position of the sensor device 2, intermediate spaces between the locking element 31, the coupling element 30 and the bracket elements 21 of the sensor device 2 can be rinsed by way of the rinsing line 34 with a saline solution, for example, and additionally also be vented.

The rinsing line 34 is connected to a rinsing connection 14 at the handle 13 (see FIG. 1), so that a rinsing liquid can be introduced via the rinsing connection 14 to the rinsing line 34.

In the illustrated exemplary embodiment, the locking element 31 of the coupling device 3 and the deflectable shaft segment 11 of the shaft 10 can be actuated by way of the actuating element 130 of the handle 13. The actuating element 130 can be rotated at the handle 13 so as to thereby cause a tensile force on the pulling element 32, and adjust the locking element 31 in the actuating direction Z with respect to the coupling element 30. Moreover, the actuating element 130 can be linearly displaced at the handle 13, so as to thus deflect the shaft segment 11, for example, by way of an assigned pull cable guided in the shaft 10, and thus guide the catheter device 1 through wound vessels.

In the illustrated exemplary embodiment, a securing element 131 is arranged at the handle 13, which, in a securing position, prevents a rotation of the actuating element 130, and thus an (inadvertent) detachment of the sensor device 2 from the coupling device 3 (but allows a linear displacement of the actuating element 130 for actuation of the deflectable shaft segment 11). The securing element 131 can be removed to be able to rotate the actuating element 130.

FIGS. 10A to 10J show a possible procedure for implanting a sensor device 2 in a patient, using the catheter device 1.

As is apparent from FIG. 1, a sheath introducer 12 is arranged at the shaft 10 of the catheter device 1, which is used to introduce the catheter device 1, together with the coupled sensor device 2, into a sheath 4, as is illustrated in FIGS. 10A to 10E. The sheath 4 serves as an access to the patient and is placed in such a way that, by way of the sheath 4, the catheter device 1, together with the coupled sensor device 2, can be guided to the human heart H, for example, as is apparent from FIGS. 10F to 10J.

Figure 10B:
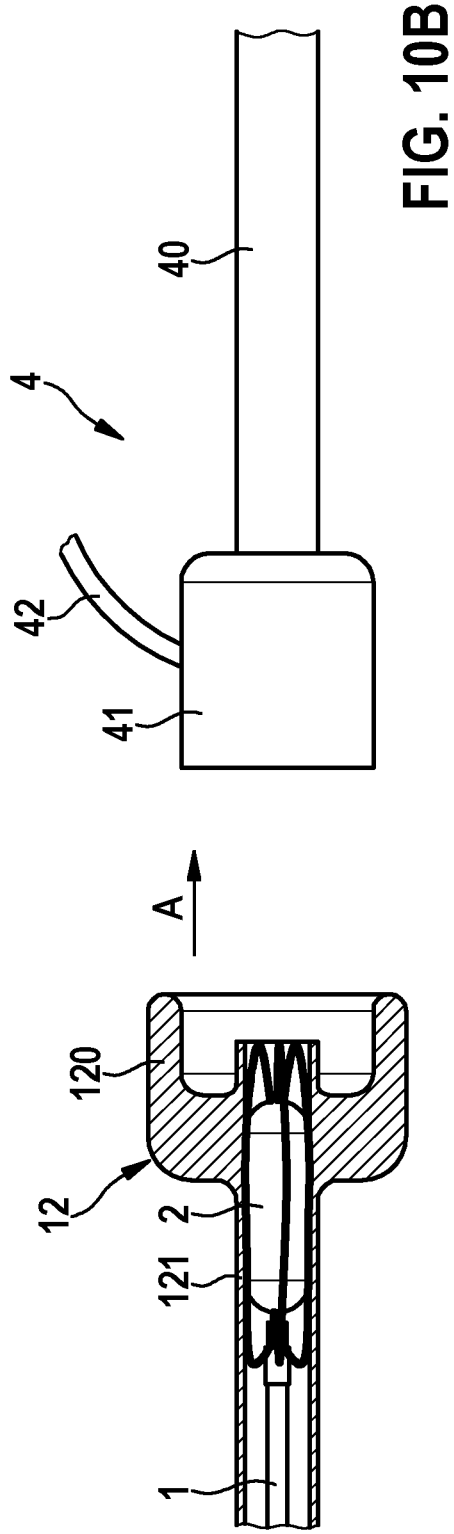

The sheath 4 is accessible from outside the patient. For the introduction of the catheter device 1, together with the coupled sensor device 2, the sensor device 2 is initially, as is apparent from FIG. 10A in the transition to FIG. 10B, pulled into the sheath introducer 12 on the side of an attachment piece 120, so that the bracket elements 21 of the sensor device 2 are folded in, and the sensor device 2 ends up inside a receiving shaft 121 of the sheath introducer 12 (FIG. 10B)

At the inlet of the insertion support 41, the sheath 4 comprises a sealing element 410 (sealing lips), through which the catheter device 1 enters during the introduction into the sheath 4 and which seals a transition to the outside.

Figure 10C:
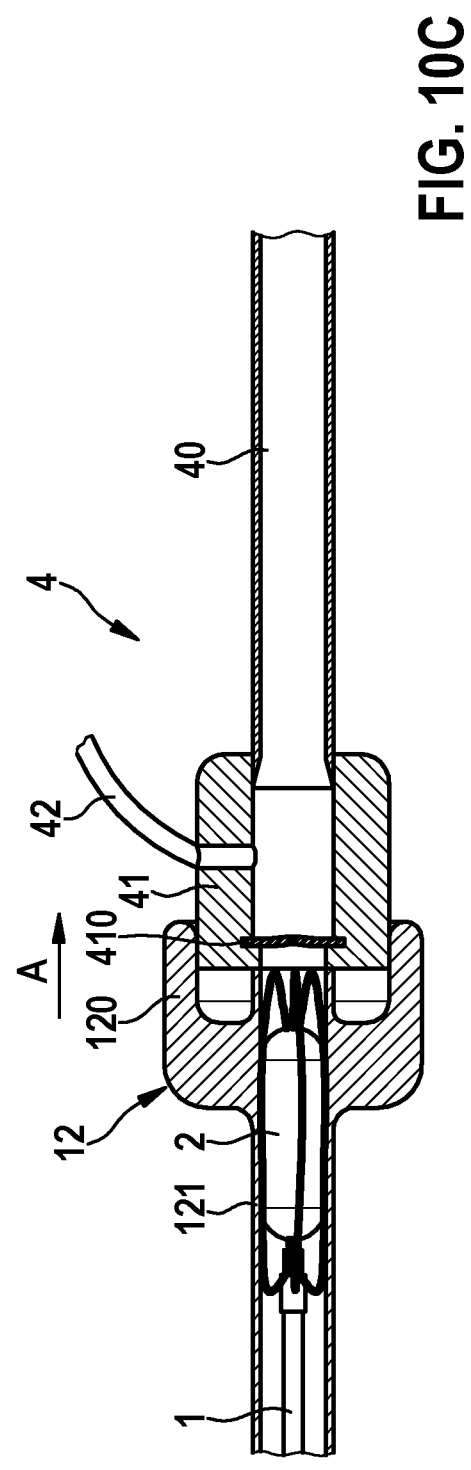
Figure 10D:
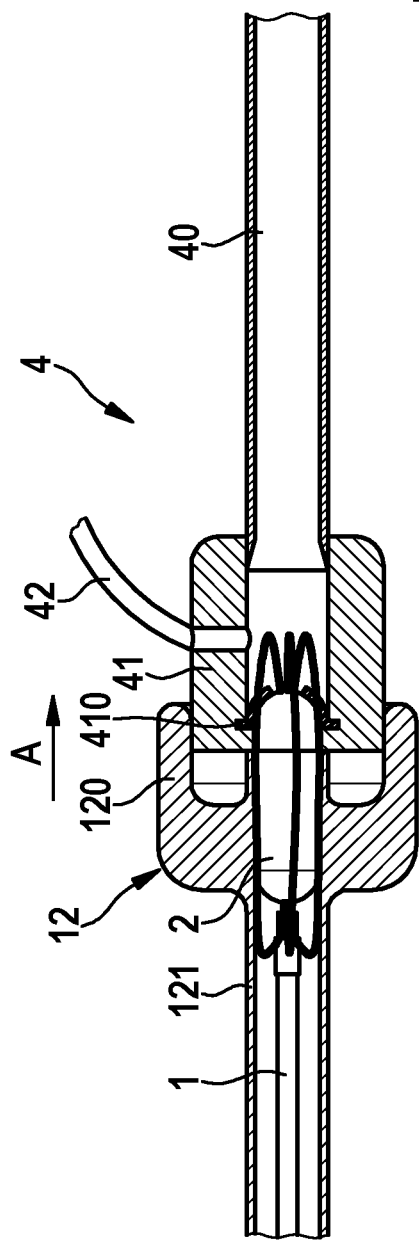
Figure 10E:
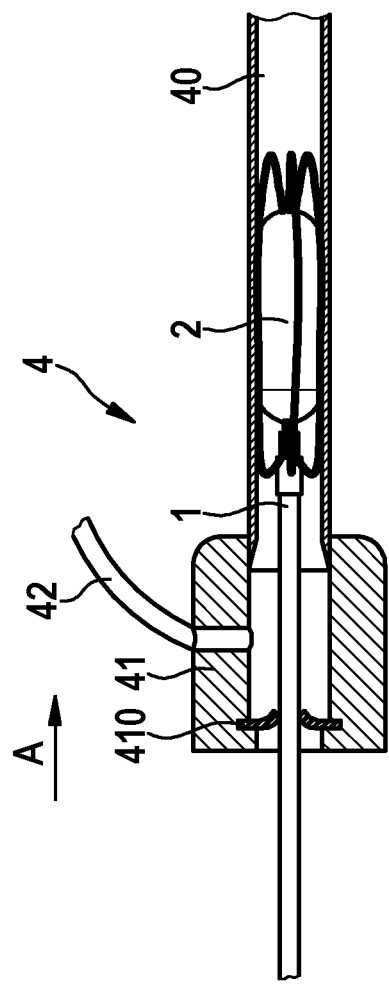

The sheath introducer 12, together with the sensor device 2 accommodated therein, is now attached with the attachment piece 120 to an insertion support 41 of the sheath 4, so that an inner channel of the receiving shaft 121 of the sheath introducer 12 is aligned with a sheath shaft 40 of the sheath 4 (FIG. 10C). The bracket elements 21 bent distally in round loops gently push the sealing element 410 of the sheath valve aside. After the sensor device 2 has passed, the sealing element 410 sealingly encloses the shaft segments that have been pushed forward.

Figure 10F:
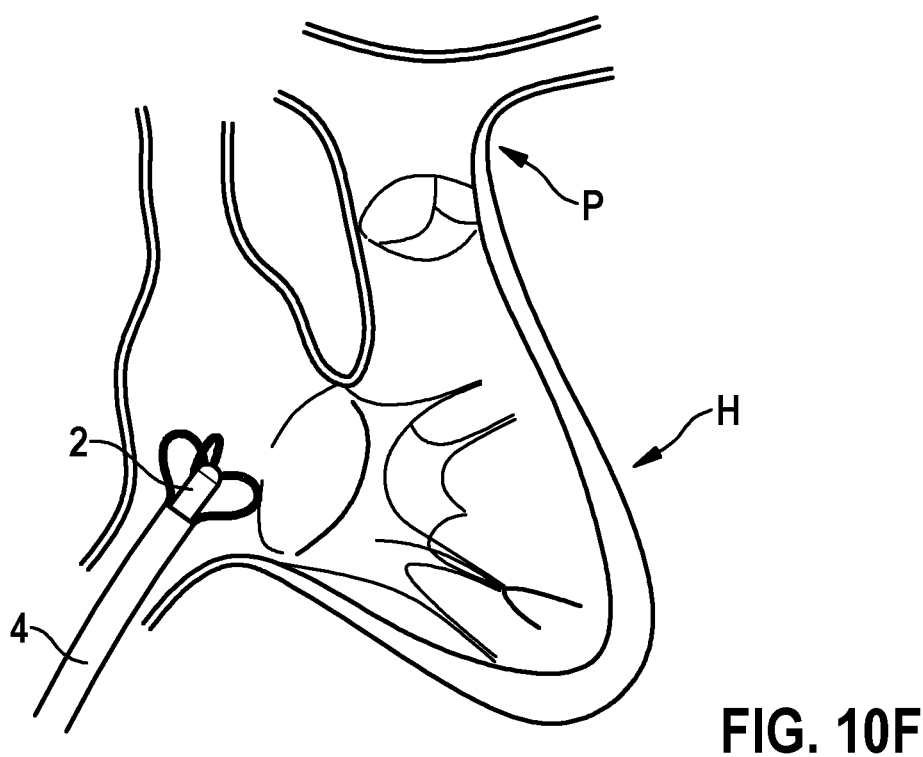
Figure 10G:
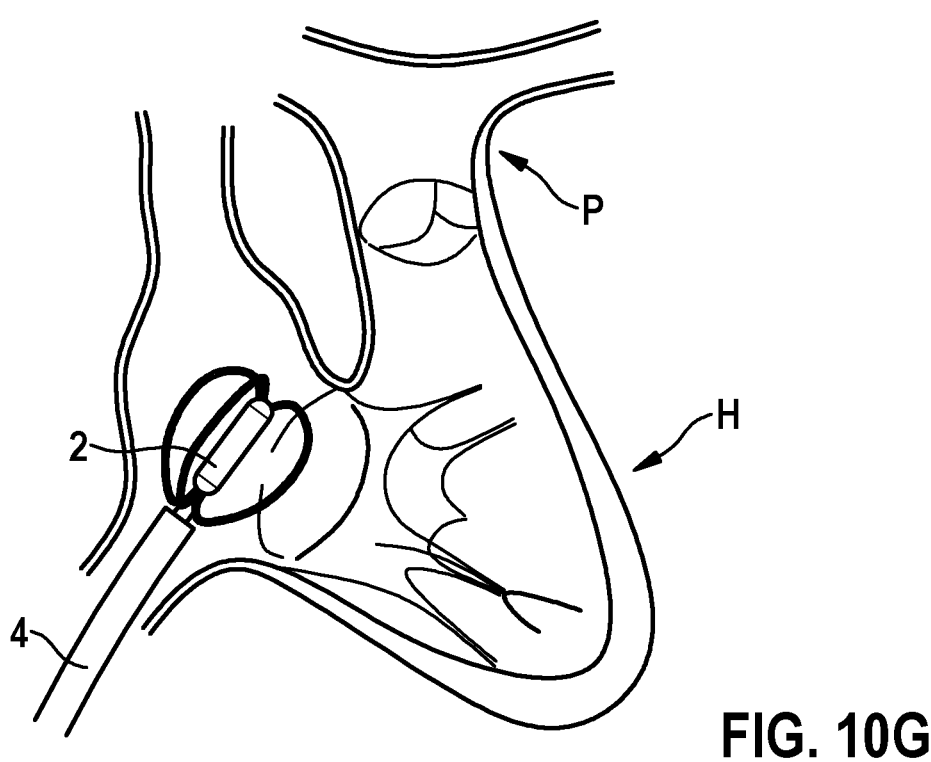
Figure 10H:
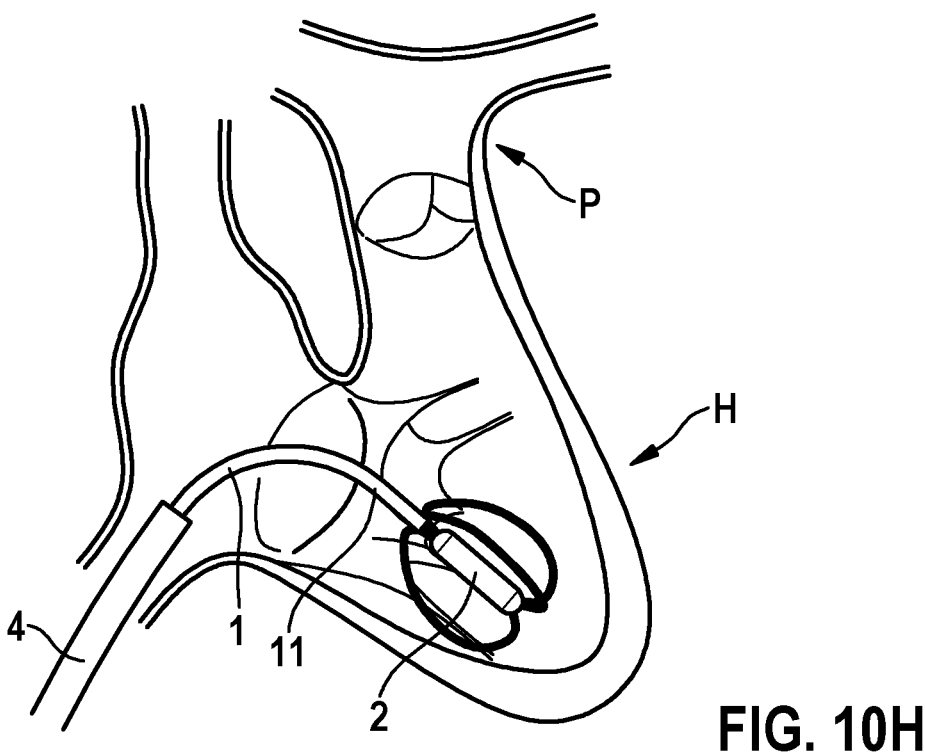

Due to the insertion of the catheter device 1, together with the coupled sensor device 2, in an introduction direction A into the sheath shaft 40, the sensor device 2 is now moved into the sheath shaft 40 (FIGS. 10D and 10E), and can thus be guided through the sheath 4 into the vessel in which the sensor device 2 is to be placed (the human heart H in the case shown by way of example), as is apparent from FIG. 10F.

In the case shown by way of example, the sensor device 2 is to be placed in the region of the pulmonary artery P. For this purpose, the catheter device 1, together with the distally coupled sensor device 2, is guided on the outlet side of the sheath 4 through the human heart H and, with a deflection of the deflectable shaft segment 11, into the region of the pulmonary artery P until an intended implantation location of the sensor device 2 has been reached (see FIG. 10G to FIG. 10J).

Figure 10I:
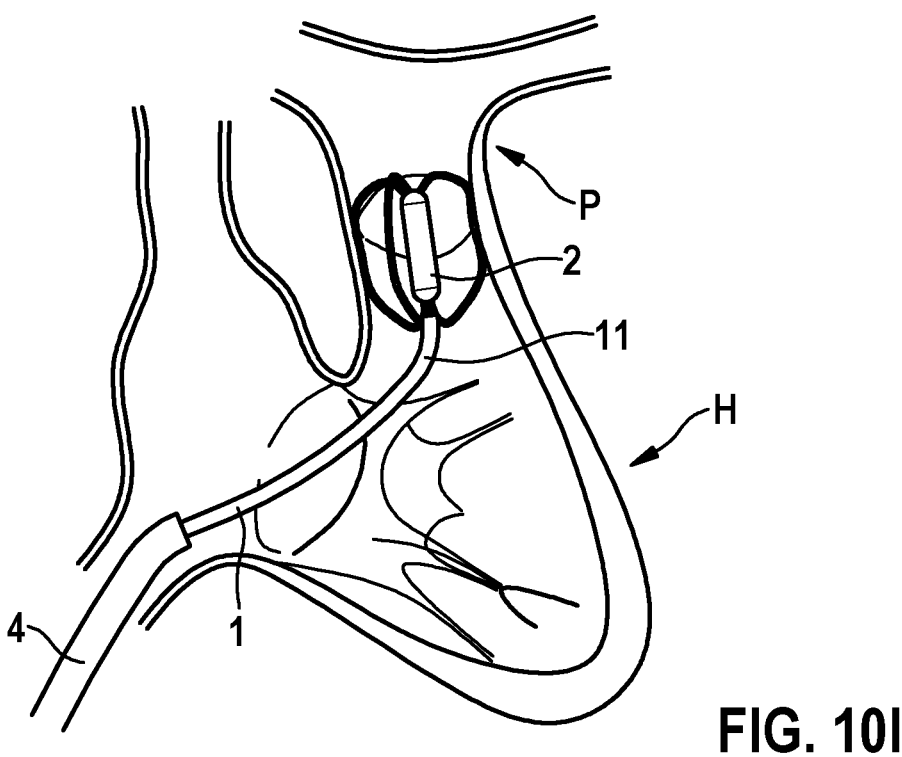
Figure 10J:
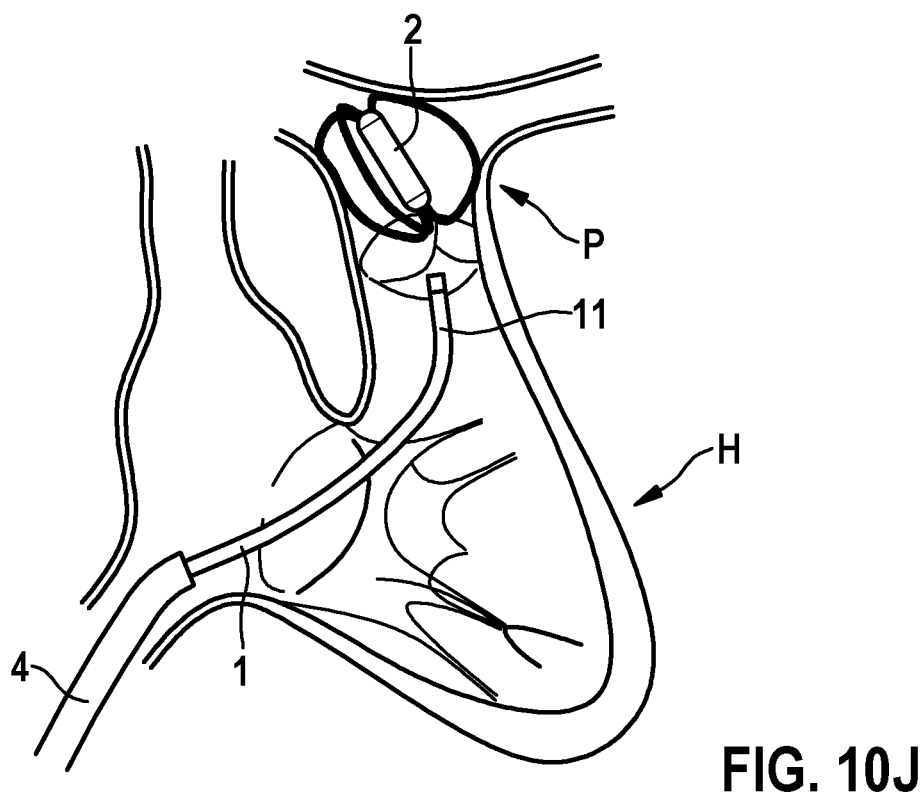

In particular, the sensor device 2 can exit the sheath 4 in the right atrium (FIG. 10F). Upon exiting the sheath 4, the bracket elements 21 deploy, as is apparent in the transition from FIG. 10F to FIG. 10G. In this state, the sensor device 2 can be checked (for example, using suitable imaging methods), wherein the sensor device 2 can be retracted when a fault of or damage to the sensor device 2 is detected. By way of the catheter device 1, the sensor device 2 is now maneuvered, for example, through the tricuspid valve, into the right ventricle (FIG. 10H), and the sensor device 2 is introduced along the anterior ventricular wall into the pulmonary valve, with deflection of the deflectable shaft segment 11 (FIG. 10I). The bracket elements 21 at the sensor device 2 prevent the catheter device from pushing behind the tendinous chords (chordae tendineae) of the tricuspid valve and possibly damaging these. After the pulmonary valve has been overcome, the sensor device 2 is advanced to the desired position in the pulmonary valve P (FIG. 10J). When an intended location has been reached, the coupling device 3 can be unlocked to decouple the sensor device 2. The sensor device 2 thus remains at the intended location thereof. The catheter device 1 can be retracted.

If it is established, for example, by way of imaging, that the sensor device 2 has not been placed correctly, the sensor device 2 can be gripped again by way of the catheter device 1 and the coupling device 3 arranged thereon, so as to correct the position of the sensor device 2.

Using the catheter device 1, an implanted sensor device 2 can be removed from the human body again, if necessary.

In addition, a rinsing line 42 is arranged at the insertion support 41, which is used to rinse the sheath shaft 40 during the introduction of the catheter device 1, together with the coupled sensor device 2, through the sheath 4.

Figure 11:
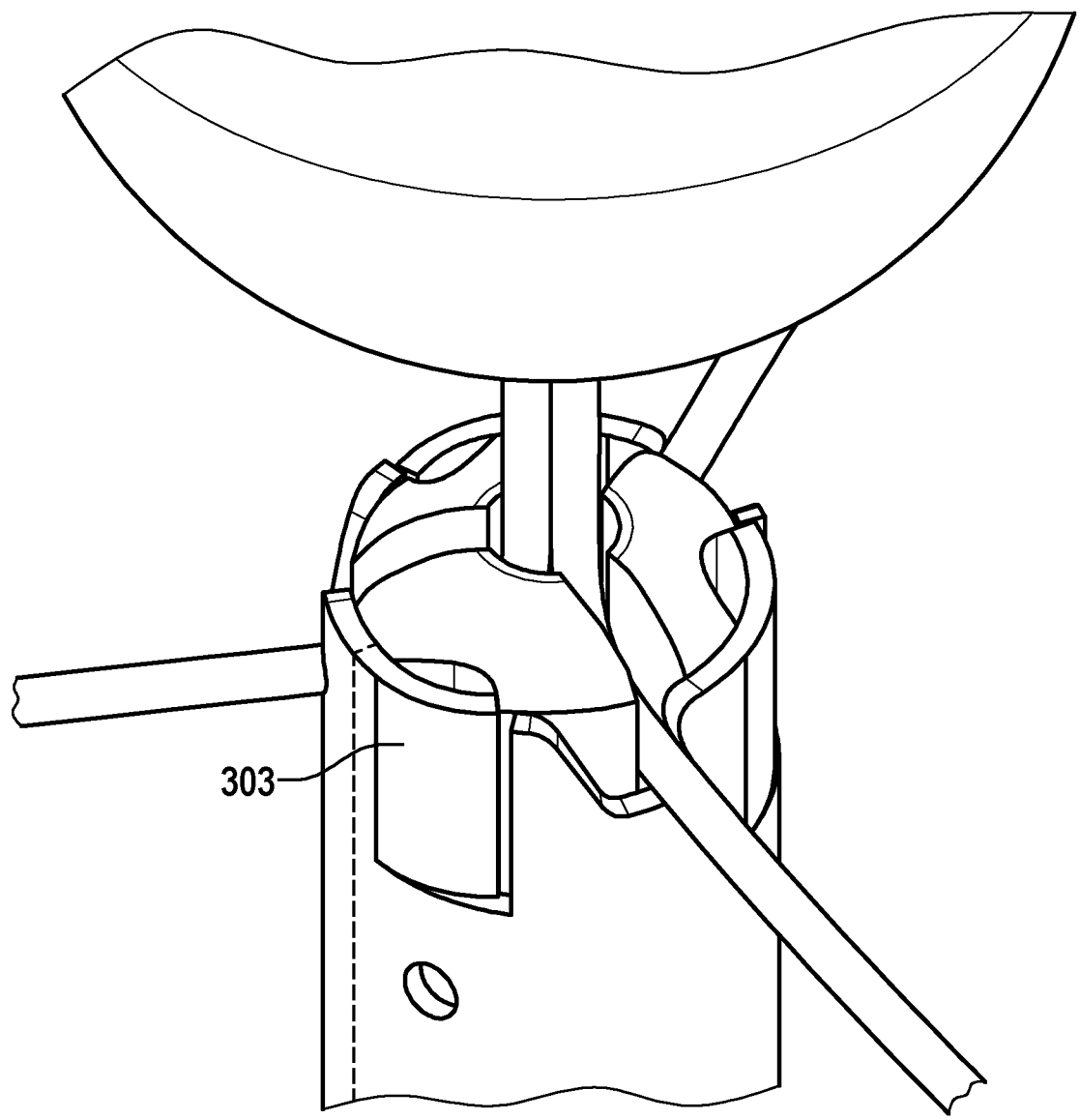
FIGS. 11 and 12 show another embodiment of the sensor device at the coupling device based on FIGS. 4 and 5.
Figure 12:
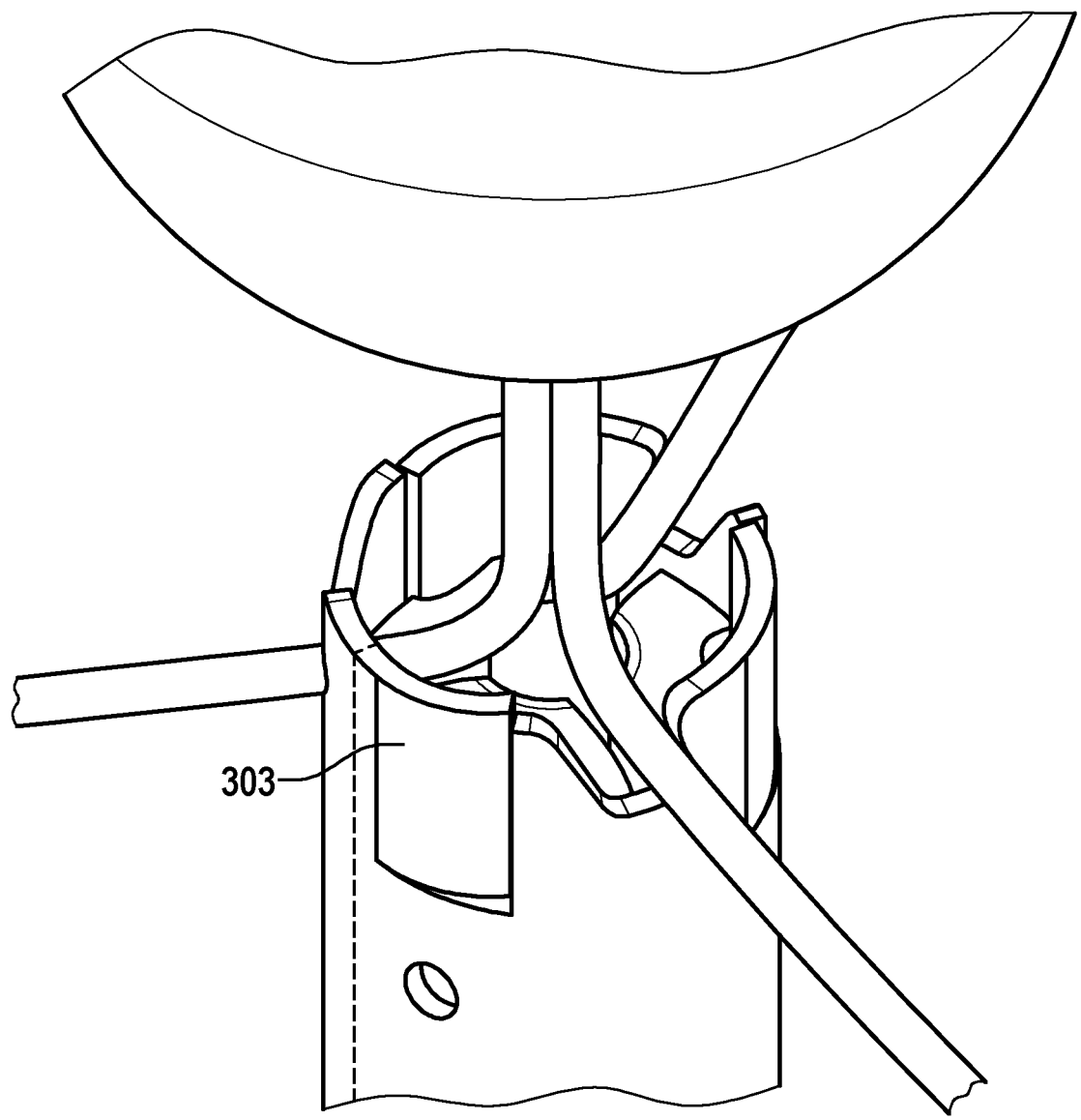

FIGS. 11 and 12 show another embodiment of the sensor device at the coupling device based on FIGS. 4 and 5. A groove between the stop element 303 and the opposing section of the housing is wider and longer than in the embodiment shown in FIGS. 4 and 5. Otherwise, all the components correspond to the components already shown in FIGS. 4 and 5 and described above.

The idea underlying the invention is not limited to the above-described exemplary embodiments, but can also be implemented in another manner.

A sensor device of the described type can comprise more or fewer than three bracket elements. It is conceivable, for example, for the sensor device to comprise only two bracket elements. It is also conceivable for the sensor device to comprise more than three bracket elements, such as four or five bracket elements.

The sensor housing can be held centrally between the bracket elements, and thus centrally in a vessel, by way of the bracket elements. However, it is also conceivable that the bracket elements hold the sensor housing not centrally, i.e., off-centered, for example close to a vessel wall.

Such a sensor device may be designed as a pressure sensor, a temperature sensor, an oxygen sensor or a flow sensor or also as another sensor and comprises a corresponding sensor system. The sensor device can function self-sufficiently in the process over an extended period of time in the implanted state, so as to transmit recorded sensor data, for example within the scope of home monitoring, such as by way of telemetry to an external device.

It will be apparent to those skilled in the art that numerous modifications and variations of the described examples and embodiments are possible in light of the above teachings of the disclosure. The disclosed examples and embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

LIST OF REFERENCE SIGNS

1 catheter device
10 shaft
100 proximal end
101 distal end
11 section (deflectable shaft segment)
12 sheath introducer
120 attachment piece
121 receiving shaft
13 handle
130 actuating element
131 securing element
14 rinsing connection
2 sensor device
20 sensor housing
21 bracket element (wire bracket)
210, 211 end
212 anchor point
3 coupling device
30 coupling element (coupling sleeve)
300 recess
301 blocking section
302 engagement section
303 stop element
304 bottom section
305 opening
306 rim
307 raised section
308 compression spring
31 locking element
310 body
311 engagement groove
312 opening
313 stop
314 channel
315 conical section
316 adhesive compound
32 pulling element
320 connecting element
321 section
33 elastic element
34 rinsing line
4 sheath
40 sheath shaft
41 insertion support
410 sealing element
42 rinsing line
A insertion direction
D detachment direction
E separation direction
Z actuating direction

I claim:

1. A catheter device for placing a sensor device, comprising:
   a shaft; and
   a coupling device, arranged at the shaft, for coupling the catheter device to the sensor device, the sensor device comprising at least one bracket element,
   wherein the coupling device comprises a coupling element and a locking element adjustable with respect to the coupling element, the coupling element comprising at least one engagement section with which the at least one bracket element of the sensor device can be brought in engagement, the locking element being designed, in a coupled position, to block the at least one bracket element at the at least one engagement section and being adjustable with respect to the coupling element so as to release the at least one bracket element for detachment from the at least one engagement section,
   wherein the coupling device comprises an elastic element, which is arranged at the coupling element and acts between the coupling element and the locking element.

2. The catheter device according to claim 1, wherein the coupling element is fixedly connected to a section of the shaft.

3. The catheter device according to claim 1, wherein the locking element is linearly adjustable along an actuating direction (Z) with respect to the coupling element.

4. The catheter device according to claim 3, wherein the coupling element is designed as a sleeve, in which the locking element is guided along the actuating direction (Z).

5. The catheter device according to claim 1, wherein the coupling element, at a rim located away from the shaft, comprises at least one recess at which the at least one engagement section is formed.

6. The catheter device according to claim 1, wherein the locking element comprises at least one engagement groove for receiving the at least one bracket element in the coupled position.

7. The catheter device according to claim 1, wherein the coupling device comprises a pulling element, which is connected to the locking element and extends along the shaft, for adjusting the locking element.

8. The catheter device according to claim 7, further comprising a handle, which is arranged at an end of the shaft that faces away from the coupling device, the handle comprising an actuating element for actuating the pulling element.

9. The catheter device according to claim 1, wherein the locking element comprises a body and a conical section, formed at the body, for interacting with the elastic element.

10. The catheter device according to claim 1, wherein the coupling element comprises a bottom section, at which the elastic element is arranged and to which the locking element is moved closer during an adjustment for detachment of the at least one bracket element from the at least one engagement section.

11. The catheter device according to claim 1, wherein the shaft comprises a deflectable shaft segment, at which the coupling device is arranged.

12. A system comprising:
a catheter device according to claim 1; and
a sensor device to be coupled to the coupling device of the catheter device.

13. The system according to claim 12, wherein the sensor device comprises a sensor housing and at least one bracket element, which is arranged at the sensor housing and, in the coupled position, engages with the at least one engagement section of the coupling element.

14. The system according to claim 13, wherein the at least one bracket element is attached with a first end to a distal side of the sensor housing, and with a second end to a proximal side of the sensor housing which faces away from the distal side.

* * * * *